US012653719B1

(12) United States Patent
Nunez

(10) Patent No.: US 12,653,719 B1
(45) Date of Patent: Jun. 16, 2026

(54) EYE AND NOSE PROTECTION ASSEMBLY

(71) Applicant: Ramon Alberto Nunez, Belleville, NJ (US)

(72) Inventor: Ramon Alberto Nunez, Belleville, NJ (US)

( * ) Notice: Subject to any disclaimer, the term of this patent is extended or adjusted under 35 U.S.C. 154(b) by 579 days.

(21) Appl. No.: 18/200,690

(22) Filed: May 23, 2023

(51) Int. Cl.
  *A61F 9/02* (2006.01)
  *A61M 16/06* (2006.01)
(52) U.S. Cl.
  CPC .............. *A61F 9/029* (2013.01); *A61F 9/027* (2013.01); *A61M 16/0672* (2014.02)
(58) Field of Classification Search
  CPC ..... A61F 9/028; A61F 9/029; A41D 13/1184; A62B 18/00; A62B 18/003; A62B 18/025; A62B 18/06; A62B 7/12; A62B 9/04; A62B 23/025; A61M 16/06; A61M 16/0627; A61M 16/0666; A61M 16/0672; A61M 2210/0612; A61M 2210/0618
  See application file for complete search history.

(56) References Cited

U.S. PATENT DOCUMENTS

| | | | |
|---|---|---|---|
| 5,033,128 A | * | 7/1991 | Torres .................... A62B 18/00 |
| | | | 2/427 |
| 5,193,534 A | * | 3/1993 | Peppler ............. A61M 16/0666 |
| | | | 128/207.18 |
| 6,532,598 B1 | | 3/2003 | Cardarelli |
| 7,077,137 B2 | | 7/2006 | Russell |
| 8,365,732 B2 | | 2/2013 | Johnstone |
| D817,477 S | | 5/2018 | Han |
| 2018/0200544 A1 | | 7/2018 | Liu |
| 2019/0314203 A1 | | 10/2019 | D'Orazio |
| 2022/0248780 A1 | | 8/2022 | Benzakin |

FOREIGN PATENT DOCUMENTS

CN          215607573 U  *  1/2022  ............ A61M 33/14

* cited by examiner

*Primary Examiner* — Joseph D. Boecker

(57) ABSTRACT

The eye and nose protection assembly is an item of personal protective equipment. The eye and nose protection assembly is a therapeutic device. The eye and nose protection assembly is adapted for use with a patient. The eye and nose protection assembly forms a protected space that protects the patient from environmental allergens. The eye and nose protection assembly incorporates an eye guard frame, a nose guard frame, and an oxygen source. The nose guard frame and the oxygen source attach to the eye guard frame. The nose guard frame and the eye guard frame form the protected space. The oxygen source feeds therapeutic oxygen into the protected space.

9 Claims, 5 Drawing Sheets

111

115

113

112

132

EYE AND NOSE PROTECTION ASSEMBLY

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of additional functions and features for eyewear. (A61F9/029)

SUMMARY OF INVENTION

The eye and nose protection assembly is an item of personal protective equipment. The eye and nose protection assembly is a therapeutic device. The eye and nose protection assembly is adapted for use with a patient. The eye and nose protection assembly forms a protected space that protects the patient from environmental allergens. The eye and nose protection assembly comprises an eye guard frame, a nose guard frame, and an oxygen source. The nose guard frame and the oxygen source attach to the eye guard frame. The nose guard frame and the eye guard frame form the protected space. The oxygen source feeds therapeutic oxygen into the protected space.

These together with additional objects, features and advantages of the eye and nose protection assembly will be readily apparent to those of ordinary skill in the art upon reading the following detailed description of the presently preferred, but nonetheless illustrative, embodiments when taken in conjunction with the accompanying drawings.

In this respect, before explaining the current embodiments of the eye and nose protection assembly in detail, it is to be understood that the eye and nose protection assembly is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the eye and nose protection assembly.

It is therefore important that the claims be regarded as including such equivalent construction insofar as they do not depart from the spirit and scope of the eye and nose protection assembly. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention.

They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
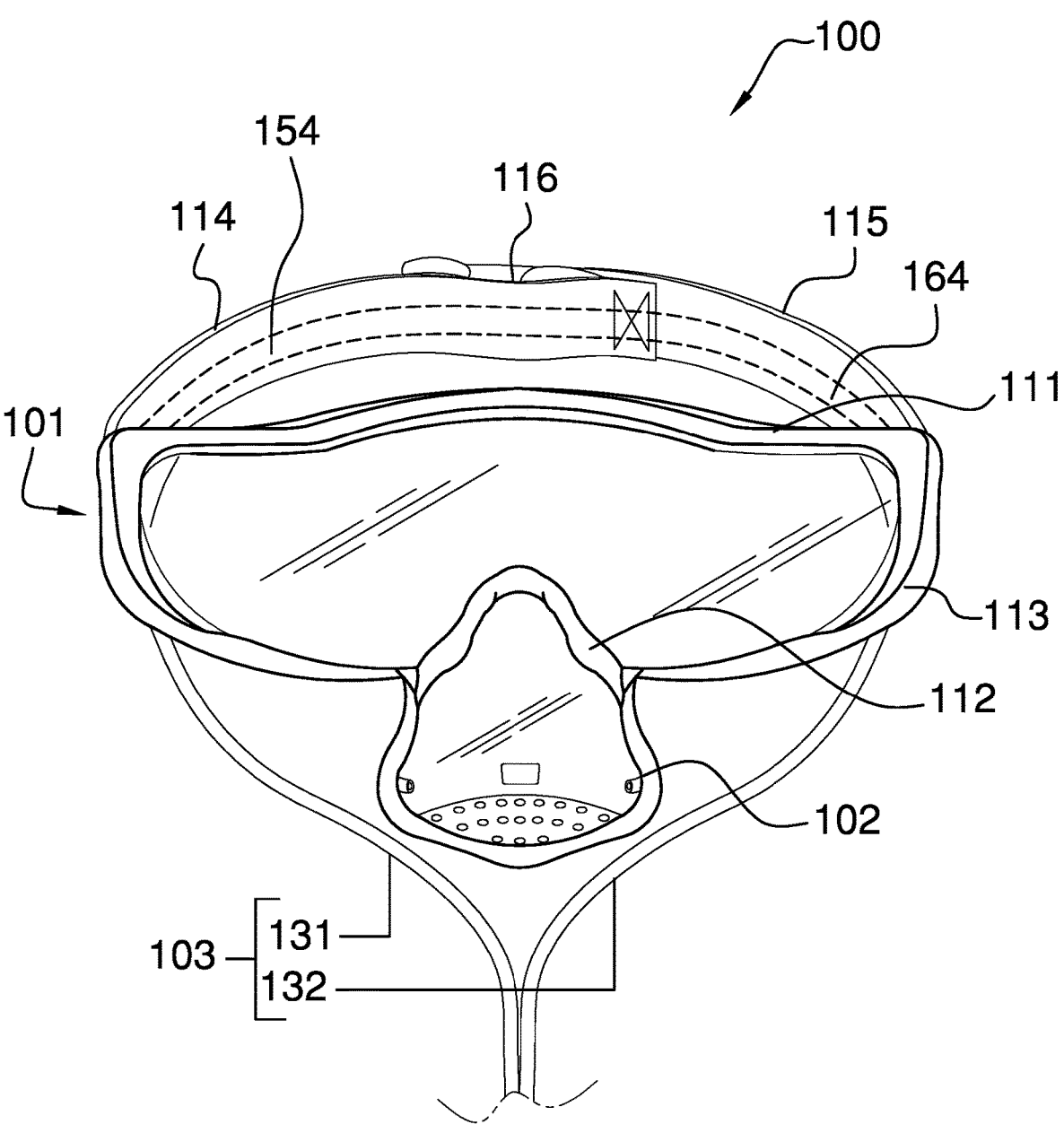
FIG. 1 is a front view of an embodiment of the disclosure.
Figure 2:
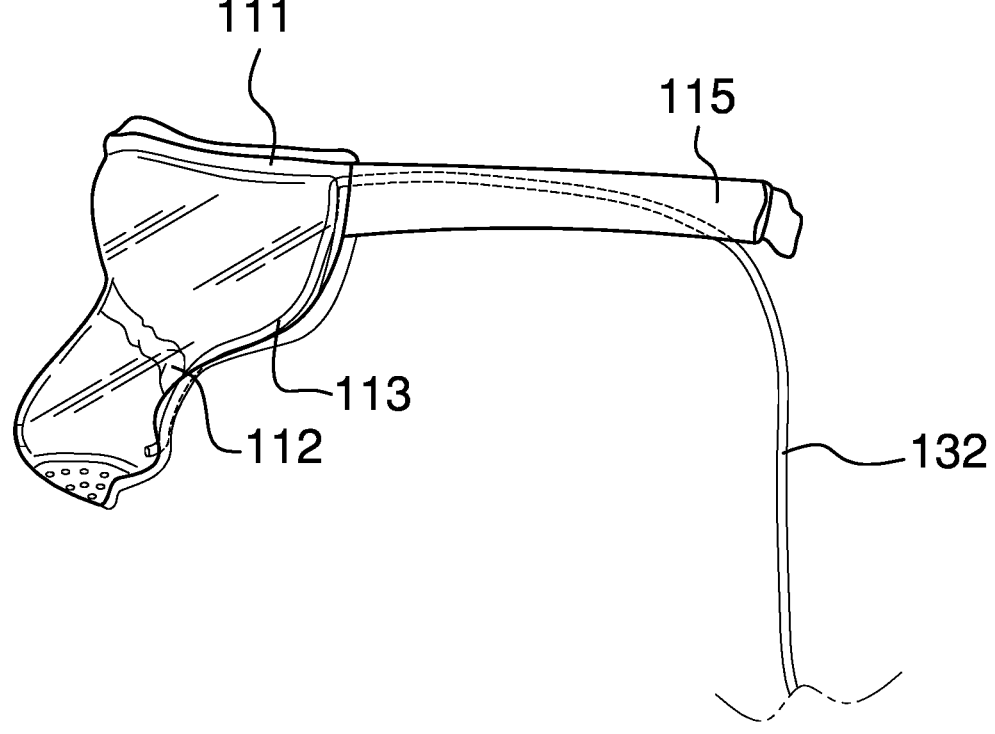
FIG. 2 is a side view of an embodiment of the disclosure.
Figure 3:
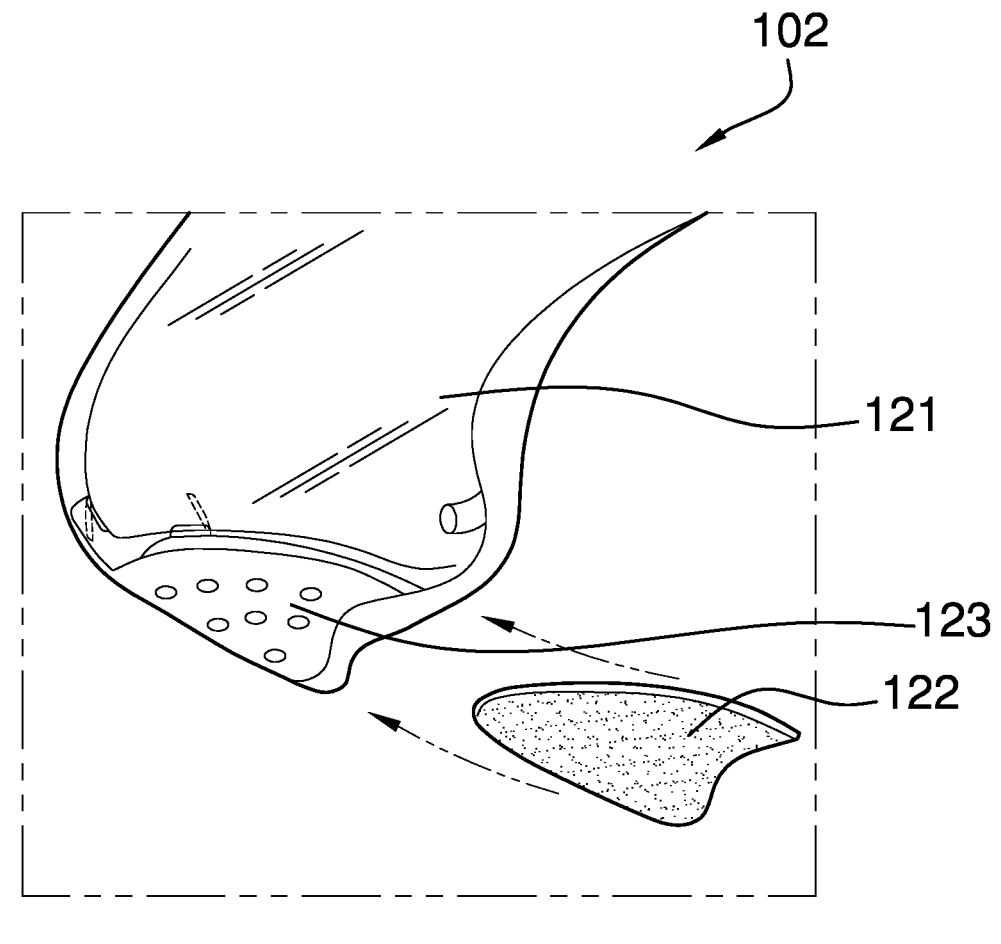
FIG. 3 is a detail view of an embodiment of the disclosure.
Figure 4:
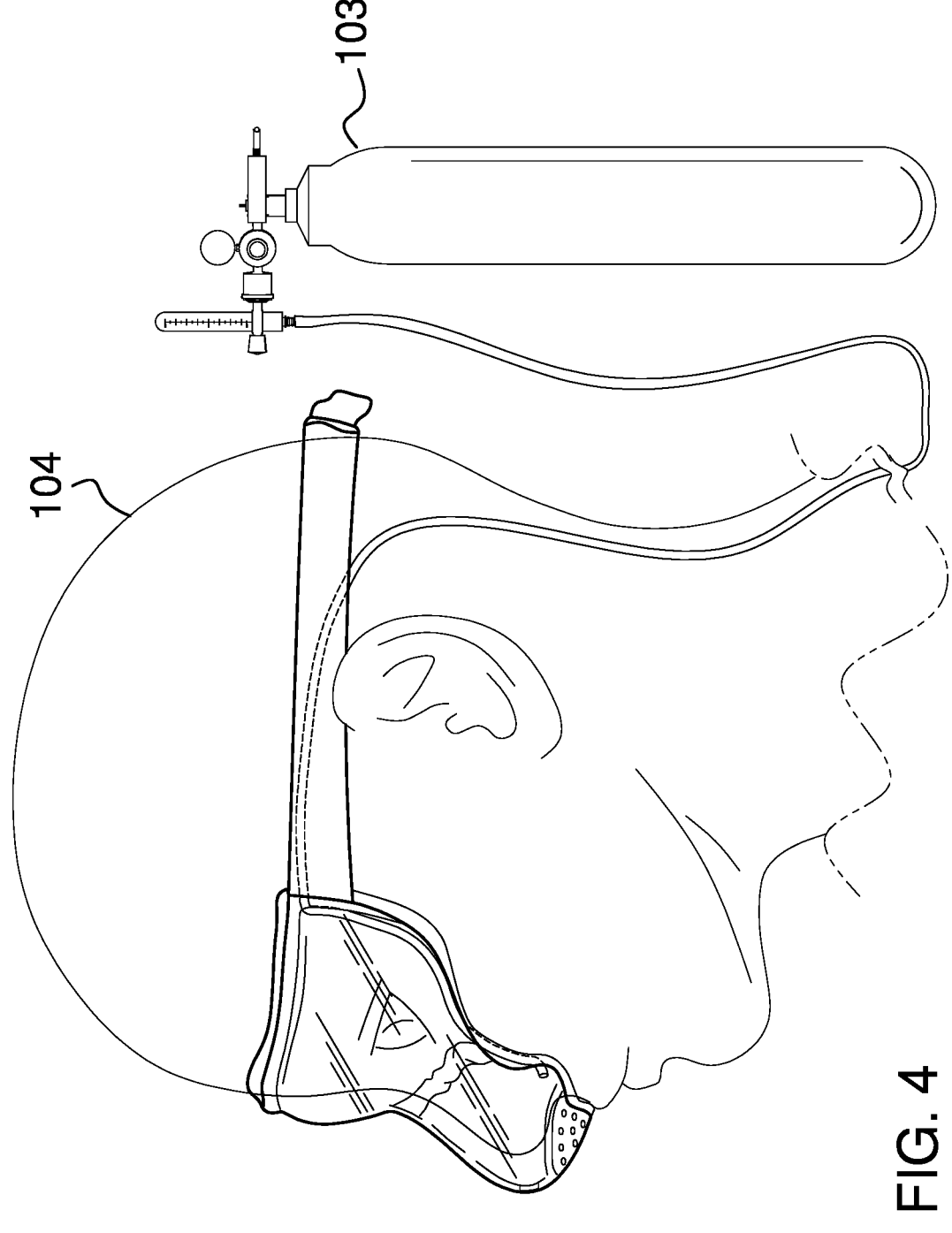
FIG. 4 is an in-use view of an embodiment of the disclosure.
Figure 5:
FIG. 5 is a perspective view of an embodiment of the disclosure.

Detailed reference will now be made to one or more potential embodiments of the disclosure, which are illustrated in FIGS. 1 through 5.

The eye and nose protection assembly 100 (hereinafter invention) is an item of personal protective equipment. The invention 100 is a therapeutic device. The invention 100 is adapted for use with a patient 104. The invention 100 forms a protected space that protects the patient 104 from environmental allergens. The invention 100 comprises an eye guard frame 101, a nose guard frame 102, and an oxygen source 103. The nose guard frame 102 and the oxygen source 103 attach to the eye guard frame 101. The nose guard frame 102 and the eye guard frame 101 form the protected space. The oxygen source 103 feeds therapeutic oxygen into the protected space.

The patient 104 is the individual who is designated to receive the services of the invention 100.

The oxygen source 103 is the structure of the invention 100 that stores, transports, and distributes the therapeutic oxygen. The oxygen source 103 provides the therapeutic oxygen that is discharged into the air that is inhaled by the patient 104.

The oxygen source 103 comprises a right hose 131 and a left hose 132. The right hose 131 is a fluid transport structure. The right hose 131 transports the therapeutic oxygen provided by the oxygen source 103 to the portion of the protected space that is formed by the nose guard frame 102. The right hose 131 discharges the transported therapeutic oxygen into the portion of the protected space that is formed by the nose guard frame 102. The left hose 132 is a fluid transport structure. The left hose 132 transports the therapeutic oxygen provided by the oxygen source 103 to the portion of the protected space that is formed by the nose guard frame 102. The left hose 132 discharges the transported therapeutic oxygen into the portion of the protected space that is formed by the nose guard frame 102.

The eye guard frame 101 forms the primary structure of the invention 100. The eye guard frame 101 forms the portion of the protected space of the invention 100 that protects the eyes of the patient 104 from allergens in the environment. The eye guard frame 101 encloses the eyes of the patient 104. The nose guard frame 102 attaches to the eye guard frame 101. The oxygen source 103 attaches to the eye guard frame 101. The eye guard frame 101 is a mechanical structure. The eye guard frame 101 is worn by a patient 104. The eye guard frame 101 secures the protected space formed by the invention 100 to the patient 104. The protected space encloses the eyes and the nose of the patient 104.

The eye guard frame 101 comprises a top bar 111, a bridge 112, an eye guard structure 113, a right temple strap 114, a left temple strap 115, and a fastening device 116. The top bar 111 forms the superior structure of the eye guard frame 101. The bridge 112 mounts the eye guard structure 113 on the nose of the patient 104. The bridge 112 and the eye guard structure 113 relate to the top bar 111 in a manner selected from the group consisting of: a) the bridge 112 and/or the eye guard structure 113 attach directly to the top bar 111; and, b) the bridge 112 and/or the eye guard structure 113 form a portion of the top bar 111. The right temple strap 114 and the left temple strap 115 attach to the top bar 111. The fastening device 116 secures the right temple strap 114 to the left temple strap 115.

The eye guard structure 113 is formed to receive a transparent lens. The transparent lens forms a transparent boundary structure. The transparent lens encloses the portion of the protected space that encloses the eyes of the patient 104. The transparent nature of the transparent lens allows the patient 104 to see through the boundary of the protected space.

The right temple strap 114 secures the eye guard frame 101 to the head of the patient 104. The right temple strap 114 secures the eye guard frame 101 to the head of the patient 104. The right temple strap 114 is a textile shaped structure. The right temple strap 114 is formed has a webbing. The right temple strap 114 is formed as a tubular textile.

The right temple strap 114 further comprises a right hose 131 rouleau 154. The right hose 131 rouleau 154 is a negative space that is formed through the right temple strap 114. The right hose 131 rouleau 154 is geometrically similar to the right hose 131. The right hose 131 rouleau 154 is sized such that the right hose 131 inserts through the right hose 131 rouleau 154. The right hose 131 rouleau 154 guides the right hose 131 from the posterior right side of the patient 104 to the nose guard frame 102. The right hose 131 discharges the transported therapeutic oxygen directly into the portion of the protected space that is formed by the nose guard frame 102.

The left temple strap 115 secures the eye guard frame 101 to the head of the patient 104. The left temple strap 115 is a textile shaped structure. The left temple strap 115 is formed has a webbing. The left temple strap 115 is formed as a tubular textile.

The left temple strap 115 further comprises a left hose 132 rouleau 164. The left hose 132 rouleau 164 is a negative space that is formed through the left temple strap 115. The left hose 132 rouleau 164 is geometrically similar to the left hose 132. The left hose 132 rouleau 164 is sized such that the left hose 132 inserts through the left hose 132 rouleau 164. The left hose 132 rouleau 164 guides the left hose 132 from the posterior right side of the patient 104 to the nose guard frame 102. The left hose 132 discharges the transported therapeutic oxygen directly into the portion of the protected space that is formed by the nose guard frame 102.

The fastening device 116 is a mechanical device that attaches the left temple strap 115 to the right temple strap 114. The fastening device 116 is a detachable structure. By detachable structure is meant that the left temple strap 115 is detachable from the right temple strap 114. The fastening device 116 is an adjustable structure. By adjustable structure is meant that the fastening device 116 can adjust the span of the lengths of portion of the left temple strap 115 that is in contact with the head of the patient 104. By adjustable structure is further meant that the fastening device 116 can adjust the span of the lengths of portion of the right temple strap 114 that is in contact with the head of the patient 104. The fastening device 116 attaches the invention 100 to the head of the patient 104 by binding the left temple strap 115 and the right temple strap 114 to the head of the patient 104.

The nose guard frame 102 forms the portion of the protected space of the invention 100 that protects the nose of the patient 104 from allergens in the environment. The nose guard frame 102 encloses the nose of the patient 104. The nose guard frame 102 filters the air the is inhaled by the patient 104. The nose guard frame 102 receives the therapeutic oxygen from the oxygen source 103 through the eye guard frame 101. The nose guard frame 102 mixes the therapeutic oxygen into the air inhaled by the patient 104. The nose guard frame 102 comprises a nose guard shell 121 and a surface filter 122.

The nose guard shell 121 is a fluid impermeable barrier. The nose guard shell 121 is geometrically similar to the nose of the patient 104. The nose guard shell 121 attaches to the bridge 112 of the eye guard frame 101 such that the nose guard shell 121 encloses the exterior surface of the nose of the patient 104. The nose guard shell 121 routes the flow an air that is inhaled by the patient 104 through the surface filter 122. The nose guard shell 121 further comprises a surface filter 122 mount 123.

The surface filter 122 mount 123 is a mechanical structure. The surface filter 122 mount 123 forms a mount that attaches the surface filter 122 to the nose guard shell 121. The surface filter 122 removably inserts into the surface filter 122 mount 123. The surface filter 122 mount 123 positions the surface filter 122 within the nose guard frame 102 such that the air that is inhaled by the patient 104 passes through and is filtered by the surface filter 122.

The surface filter 122 is a filter. The surface filter 122 forms a fluid permeable barrier that allows a flow of air to enter the protected space formed by the nose guard frame 102. The surface filter 122 filters the air that enters the nose guard frame 102 for inhalation by the patient 104. The surface filter 122 filters the allergens from the air that is inhaled by the patient 104.

The following definitions were used in this disclosure:

Align: As used in this disclosure, align refers to an arrangement of objects that are: 1) arranged in a straight plane or line; 2) arranged to give a directional sense of a plurality of parallel planes or lines; or, 3) a first line or curve is congruent to and overlaid on a second line or curve.

Anterior: As used in this disclosure, anterior is a term that is used to refer to the front side or direction of a structure. When comparing two objects, the anterior object is the object that is closer to the front of the structure.

Barrier: As used in this disclosure, a barrier is a physical obstacle that forms a boundary between a first space and a second space. The barrier prevents the passage of an object between the first space and the second space.

Bind: As used in this disclosure, to bind is a verb that means to tie or secure a first object to a second object using a strap, cord or webbing. Bind can also mean to tie or secure a plurality of similar first objects together by wrapping a second object around the plurality of similar first objects.

Cant: As used in this disclosure, a cant is an angular deviation from one or more reference lines (or planes) such as a vertical line (or plane) or a horizontal line (or plane).

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or a prism. The center axis of a prism is the line that joins the center point of the first congruent face of the prism to the center point of the second corresponding congruent face of the prism. The center axis of a pyramid refers to a line formed through the apex of the pyramid that is perpendicular to the base of the pyramid. When the center axes of two cylinder, prism or pyramidal structures share the same line they are said to be aligned. When the center axes of two cylinder, prism or pyramidal structures do not share the same line they are said to be offset.

Composite Prism: As used in this disclosure, a composite prism refers to a structure that is formed from a plurality of structures selected from the group consisting of a prism structure and a pyramid structure. The plurality of selected structures may or may not be truncated. The plurality of prism structures are joined together such that the center axes of each of the plurality of structures are aligned. The congruent ends of any two structures selected from the group consisting of a prism structure and a pyramid structure need not be geometrically similar.

Congruent: As used in this disclosure, congruent is a term that compares a first object to a second object. Specifically, two objects are said to be congruent when: 1) they are geometrically similar; and, 2) the first object can superimpose over the second object such that the first object aligns, within manufacturing tolerances, with the second object.

Cord: As used in this disclosure, a cord is a long, thin, flexible, and prism shaped string, line, rope, or wire. Cords are made from yarns, piles, or strands of material that are braided or twisted together or from a monofilament (such as fishing line). Cords have tensile strength but are too flexible to provide compressive strength and are not suitable for use in pushing objects. String, line, cable, yarn, and rope are synonyms for cord. This definition further includes textile webbings as a type of cord.

Correspond: As used in this disclosure, the term correspond is used as a comparison between two or more objects wherein one or more properties shared by the two or more objects match, agree, or align within acceptable manufacturing tolerances.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk. In this disclosure, the congruent ends of the prism-shaped structure that forms the disk are referred to as the faces of the disk.

Elevation: As used in this disclosure, elevation refers to the span of the distance in the superior direction between a specified horizontal surface and a reference horizontal surface. Unless the context of the disclosure suggest otherwise, the specified horizontal surface is the supporting surface the potential embodiment of the disclosure rests on. The infinitive form of elevation is to elevate.

Environment: As used in this disclosure, an environment refers to the physical conditions surrounding an object. The term environment is often limited to the physical conditions that the object interacts with.

Extension Structure: As used in this disclosure, an extension structure is an inert physical structure that is used to extend or bridge the reach between any two objects.

Exterior: As used in this disclosure, the exterior is used as a relational term that implies that an object is not contained within the boundary of a structure or a space.

Eyeglasses: As used in this disclosure, eyeglasses are a pair of lenses held in a frame that are worn over the eyes. Eyeglasses are used to help with vision.

Fastener: As used in this disclosure, a fastener is a device that is used to join or affix two objects. Fasteners generally comprise a first element which is attached to the first object and a second element which is attached to the second object such that the first element and the second element join to removably attach the first object and the second object. Common fasteners include, but are not limited to, hooks, zippers, magnets, snaps, buttons, buckles, quick release buckles, or hook and loop fasteners. A fastener is often referred to as a fastening device.

Filter: As used in this disclosure, a filter is a mechanical device that is used to separate solids that are suspended in a liquid or a gas. A strainer is type of coarse filter.

Flow: As used in this disclosure, a flow refers to the passage of a fluid past a fixed point. This definition considers bulk solid materials as capable of flow.

Fluid: As used in this disclosure, a fluid refers to a state of matter wherein the matter is capable of flow and takes the shape of a container it is placed within. The term fluid commonly refers to a liquid or a gas.

Fluid Impermeable: As used in this disclosure, the term fluid impermeable refers to: a) the ability of a structure to not allow a fluid to pass through the structure; or, b) the ability of a material not absorb through the exterior surfaces of the material a fluid that the material is immersed in or exposed to.

Fluidic Connection: As used in this disclosure, a fluidic connection refers to a tubular structure that transports a fluid from a first object to a second object. Methods to design and use a fluidic connections are well-known and documented in the mechanical, chemical, and plumbing arts.

Force of Gravity: As used in this disclosure, the force of gravity refers to a vector that indicates the direction of the pull of gravity on an object at or near the surface of the earth.

Form Factor: As used in this disclosure, the term form factor refers to the size and shape of an object.

Garment: As used in this disclosure, a garment is a textile based structure that is used to cover an individual. Clothes, clothing, and apparel are synonyms for garment.

Gas: As used in this disclosure, a gas refers to a state (phase) of matter that is fluid and that fills the volume of the structure that contains it. Stated differently, the volume of a gas always equals the volume of its container.

Geometrically Similar: As used in this disclosure, geometrically similar is a term that compares a first object to a second object wherein: 1) the sides of the first object have a one to one correspondence to the sides of the second object; 2) wherein the ratio of the length of each pair of corresponding sides are equal; 3) the angles formed by the first object have a one to one correspondence to the angles of the second object; and, 4) wherein the corresponding angles are equal. The term geometrically identical refers to a situation where the ratio of the length of each pair of corresponding sides equals 1. By the term essentially geometrically similar is meant that the primary shapes of two objects are geometrically similar except that there are functional items (such as fastening devices) associated with the primary shape may not maintain the ratio for geometric similarity. By the term roughly geometrically similar is meant that the form factors between the primary shape of the two objects can vary by a factor of up to 10% when the two objects are normalized to be roughly geometrically identical.

Hook and Loop Fastener: As used in this disclosure, a hook and loop fastener is a fastener that comprises a hook surface and a loop surface. The hook surface comprises a plurality of minute hooks. The loop surface comprises a surface of uncut pile that acts like a plurality of loops. When the hook surface is applied to the loop surface, the plurality of minute hooks fastens to the plurality of loops securely fastening the hook surface to the loop surface. A note on usage: when fastening two objects the hook surface of a hook and loop fastener will be placed on the first object and the matching loop surface of a hook and loop fastener will be placed on the second object without significant regard to which object of the two objects is the first object and which of the two objects is the second object. When the hook surface of a hook and loop fastener or the loop surface of a hook and loop fastener is attached to an object this will simply be referred to as the "hook/loop surface" with the understanding that when the two objects are fastened together one of the two objects will have a hook surface and the remaining object will have the loop surface.

Horizontal: As used in this disclosure, horizontal is a directional term that refers to a direction that is either: 1) parallel to the horizon; 2) perpendicular to the local force of gravity, or, 3) parallel to a supporting surface. In cases where the appropriate definition or definitions are not obvious, the second option should be used in interpreting the specification. Unless specifically noted in this disclosure, the horizontal direction is always perpendicular to the vertical direction.

Hose: As used in this disclosure, a hose is a flexible hollow prism-shaped device that is used for transporting liquids and gases. When referring to a hose in this disclosure, the terms inner dimension and outer dimension are used as they would be used by those skilled in the plumbing arts.

Inferior: As used in this disclosure, the term inferior refers to a directional reference that is parallel to and in the same direction as the force of gravity when an object is positioned or used normally.

Interior: As used in this disclosure, the interior is used as a relational term that implies that an object is contained within the boundary of a structure or a space.

Lateral: As used in this disclosure, lateral refers to a directional sense or location of the body. Specifically, lateral refers to an object or a side of an object that is proximal to the side or that is distal from the medial axis of the body.

Left and Right: As used in this disclosure, the terms left and right are directional references associated with an object. The object is further defined with an anterior surface and a posterior surface. The terms left and right are standardized naming conventions for the lateral directions of the object. The terms left and right use the human body for the initial definition of the orientation. Specifically, when a human body is viewed from posterior side towards the anterior side, the left side of the human body is the lateral side of the human body that contains the heart. The right side of the human body is the lateral side of the body that contains the bulk of the liver. The left and right sides of the human body remain unchanged by changes to the direction from which the human body is viewed. The left side of any object is the same side as the left side of the human body when the object is viewed from posterior side towards the anterior side. The right side of any object is the same side as the right side of the human body when the object is viewed from posterior side towards the anterior side. The left and right sides of the object remain unchanged by changes to the direction from which the object is viewed.

Lens: As used in this disclosure, a lens is a transparent substance through which electromagnetic radiation can pass. The lens refracts the electromagnetic radiation as it passes through the lens. A lens may or may not be formed with curved surfaces that are used to concentrate or disperse the electromagnetic radiation that travels through the lens. A lens can also project a focused image on a surface known as a virtual image. A lens may also be used to change the apparent size of the virtual image. A magnifying lens (also known as a magnifying glass) is a lens that increase the apparent size of a virtual image. A contact lens is a lens that is worn directly on the eye of a patient.

Liquid: As used in this disclosure, a liquid refers to a state (phase) of matter that is fluid and that maintains, for a given pressure, a fixed volume that is independent of the volume of the container.

Load: As used in this disclosure, the term load refers to an object upon which a force is acting or which is otherwise absorbing energy in some fashion. Examples of a load in this sense include, but are not limited to, a mass that is being moved a distance or an electrical circuit element that draws energy. The term load is also commonly used to refer to the forces that are applied to a stationary structure.

Load Path: As used in this disclosure, a load path refers to a chain of one or more structures that transfers a load generated by a raised structure or object to a foundation, supporting surface, or the earth.

Mask: As used in this disclosure, a mask is a covering for the face of a person. A mask that filters, routes, and/or concentrates a flow of gas to the nose and mouth of a patient is called a respiratory mask.

Mount: As used in this disclosure, a mount is a mechanical structure that attaches or incorporates an object into a load path.

Negative Space: As used in this disclosure, negative space is a method of defining an object through the use of open or empty space as the definition of the object itself, or, through the use of open or empty space to describe the boundaries of an object.

One to One: When used in this disclosure, a one to one relationship means that a first element selected from a first set is in some manner connected to only one element of a second set. A one to one correspondence means that the one to one relationship exists both from the first set to the second set and from the second set to the first set. A one to one fashion means that the one to one relationship exists in only one direction.

Oxygen: As used in this disclosure, oxygen (CAS 7782-44-7) refers to the element with atomic number 8 in the periodic table. The chemical abbreviation for oxygen is 02. Oxygen is a diatomic element.

Pan: As used in this disclosure, a pan is a hollow and prism-shaped containment structure. The pan has a single open face. The open face of the pan is often, but not always, the superior face of the pan. The open face is a surface selected from the group consisting of: a) a congruent end of the prism structure that forms the pan; and, b) a lateral face of the prism structure that forms the pan. A semi-enclosed pan refers to a pan wherein the closed end of prism structure of the pan and/or a portion of the closed lateral faces of the pan are open.

Patient: As used in this disclosure, a patient is a person who is designated to receive a medical treatment, therapy, or service. The term patient may be extended to an animal when used within the context of the animal receiving veterinary treatment or services.

Perimeter: As used in this disclosure, a perimeter is one or more curved or straight lines that bounds an enclosed area on a plane or surface. The perimeter of a circle is commonly referred to as a circumference.

Pedestal: As used in this disclosure, a pedestal is an intermediary load bearing structure that forms a load path between two objects or structures.

Personal Protective Equipment: As used in this disclosure, personal protective equipment refers to the use of protective garments or protective equipment that is designed to protect the wearer's body from injury. Personal protective equipment may be designed for occupational protection, including, but not limited to, equipment to protect military, police, or firefighting personnel, or may be designed to provide protection in sports or recreational activities, including, but not limited to, equipment to protect participants in football, hockey, or soccer activities.

Phase: As used in this disclosure, phase refers to the state of the form of matter. The common states of matter are solid, liquid, gas, and plasma.

Posterior: As used in this disclosure, posterior is a term that is used to refer to the side of an object that is distal or in the opposite direction of the anterior side. When comparing two items, the posterior item is the item that is distal from the anterior of the object.

Primary Shape: As used in this disclosure, the primary shape refers to a description of the rough overall geometric shape of an object that is assembled from multiple components or surfaces.

Primary Structure: As used in this disclosure, a primary structure refers to the component of an object that the other components attach to. The primary structure is also called the base structure.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Protected Space: As used in this disclosure, a protected space is a negative space within which an object is stored. The protected space is enclosed by a barrier structure that: a) prevents damage to the object contained within the protected space; b) maintains conditions that are appropriate for the object; c) protects the object within the protected space from potential dangers that are outside of the protected space; or, d) maintains the privacy of the object within the protected space.

Reach: As used in this disclosure, reach refers to a span of distance between any two objects.

Rigid Structure: As used in this disclosure, a rigid structure is a solid structure formed from an inelastic material that resists changes in shape. A rigid structure will permanently deform as it fails under a force. See bimodal flexible structure.

Rotation: As used in this disclosure, rotation refers to the cyclic movement of an object around a fixed point or fixed axis. The verb of rotation is to rotate.

Rouleau: As used in this disclosure, a rouleau is a tube or channel that is formed on a textile or sheeting. The plural of rouleau is rouleaux.

Sheath: As used in this disclosure, a sheath is a structure that is used to enclose an object and from which the object may be inserted and withdrawn.

Solid: As used in this disclosure, a solid refers to a state (phase) of matter that: 1) has a fixed volume; and, 2) does not flow.

Strap: As used in this disclosure a strap is a strip of leather, cloth, or other flexible material, often with a buckle, that is used to fasten, secure, carry, or hold onto something.

Superior: As used in this disclosure, the term superior refers to a directional reference that is parallel to and in the opposite direction of the force of gravity when an object is positioned or used normally.

Supporting Surface: As used in this disclosure, a supporting surface is a horizontal surface upon which an object is placed and to which the load of the object is transferred. This disclosure assumes that an object placed on the supporting surface is in an orientation that is appropriate for the normal or anticipated use of the object.

Surface Filter: As used in this disclosure, a surface filter is a type of filter wherein the fluid is passed through a surface or membrane, such as a screen or paper that allows for the passage of the fluid but blocks the passage of larger particles that may be suspended in the fluid. The construction of a surface filter would allow for the passage of the fluid through several filter surfaces in one filtration unit.

Textile: As used in this disclosure, a textile is a material that is woven, knitted, braided or felted. Synonyms in common usage for this definition include fabric and cloth. The two surfaces of the textile with the greatest surface area are called the faces of the textile.

Therapeutic: As used in this disclosure, therapeutic is an adjective that refers to a medical, ameliorative, or hygienic substance, process, procedure, or device.

Transparent: As used in this disclosure, transparent refers to a material that allows light to pass through the material without significant scattering such that an object can be clearly seen through the material.

Tube: As used in this disclosure, a tube is a hollow prism-shaped device formed with two open congruent ends. The tube is used for transporting liquids (including bulk solids) and gases. The line that connects the center of the first congruent face of the prism to the center of the second congruent face of the prism is referred to as the center axis of the tube or the centerline of the tube. When two tubes share the same centerline they are said to be aligned. When the centerlines of two tubes are perpendicular to each other, the tubes are said to be perpendicular to each other. In this disclosure, the terms inner dimensions of a tube and outer dimensions of a tube are used as they would be used by those skilled in the plumbing arts.

Tubular Textile: As used in this disclosure, a tubular textile is a textile that is woven, knitted, or braided into a seamless tube like shape.

Vertical: As used in this disclosure, vertical refers to a direction that is either: 1) perpendicular to the horizontal direction; 2) parallel to the local force of gravity; or, 3) when referring to an individual object the direction from the designated top of the individual object to the designated bottom of the individual object. In cases where the appropriate definition or definitions are not obvious, the second option should be used in interpreting the specification. Unless specifically noted in this disclosure, the vertical direction is always perpendicular to the horizontal direction.

Webbing: As used in this disclosure, a webbing is strong, close woven or knitted fabric that is used for straps or belting. As used in this disclosure, webbing is a fully formed material that is only cut to length for use. Webbing is not formed by cutting broader materials into strips. Webbings have tensile strength but are too flexible to provide compressive strength and are not suitable for use in pushing objects. The shape of a webbing is approximated by a rectangular disk shape. The two surfaces of a webbing with the greatest surface area are called the faces of the webbing.

With respect to the above description, it is to be realized that the optimum dimensional relationship for the various components of the invention described above and in FIGS. 1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. An eye and nose protection assembly comprising an eye guard frame, a nose guard frame, and an oxygen source;
   wherein the nose guard frame and the oxygen source attach to the eye guard frame;
   wherein the oxygen source comprises a right hose and a left hose;
   wherein the right hose transports and discharges therapeutic oxygen provided by the oxygen source to a portion of a protected space that is formed by the nose guard frame, the protected space adapted to enclose the eyes and the nose of a patient;
   wherein the left hose transports and discharge the therapeutic oxygen provided by the oxygen source to the portion of the protected space that is formed by the nose guard frame;
   wherein the nose guard frame forms the portion of the protected space of the eye and nose protection assembly that is adapted to protect and enclose the nose of the patient;

wherein the oxygens source directly feeds the therapeutic oxygen into the portion of the protected space, formed by the nose guard frame, via the eye guard frame;
   wherein the nose guard frame is adapted to mix the therapeutic oxygen into air that is adapted to be inhaled by the patient.

2. The eye and nose protection assembly according to claim 1
   wherein the oxygen source is the structure of the eye and nose protection assembly that stores, transports, and distributes the therapeutic oxygen;
   wherein the oxygen source provides the therapeutic oxygen that is discharged into the air that is inhaled by the patient.

3. The eye and nose protection assembly according to claim 2
   wherein the eye guard frame forms the primary structure of the eye and nose protection assembly;
   wherein the eye guard frame forms the portion of the protected space of the eye and nose protection assembly that is adapted to protect the eyes of the patient;
   wherein the eye guard frame is adapted to enclose the eyes of the patient;
   wherein the nose guard frame attaches to the eye guard frame.

4. The eye and nose protection assembly according to claim 3
   wherein the eye guard frame is a mechanical structure;
   wherein the eye guard frame is adapted to be worn by the patient;
   wherein the eye guard frame is adapted to secure the protected space formed by the eye and nose protection assembly to the patient.

5. The eye and nose protection assembly according to claim 4
   wherein the eye guard frame comprises a top bar, a bridge, an eye guard, a right temple strap, and a left temple strap;
   wherein the right temple strap and the left temple strap attach to the top bar;
   wherein the eye guard is formed to receive a transparent lens;
   wherein the transparent lens forms a transparent boundary structure;
   wherein the transparent lens is adapted to enclose the portion of the protected space that encloses the eyes of the patient;
   wherein the right temple strap is adapted to secure the eye guard frame to the head of the patient;
   wherein the left temple strap is adapted to secure the eye guard frame to the head of the patient.

6. The eye and nose protection assembly according to claim 5
   wherein the nose guard frame comprises a nose guard shell and a surface filter;
   wherein the nose guard shell is a fluid impermeable barrier;
   wherein the nose guard shell attaches to the bridge of the eye guard frame such that the nose guard shell is adapted to enclose the exterior surface of the nose of the patient;
   wherein the nose guard shell is adapted to route a flow of the air that is inhaled by the patient through the surface filter;
   wherein the nose guard shell further comprises a surface filter mount;
   wherein the surface filter mount is a mechanical structure;

wherein the surface filter mount forms a mount that attaches the surface filter to the nose guard shell;

wherein the surface filter removably inserts into the surface filter mount;

wherein the surface filter mount is adapted to position the surface filter within the nose guard frame such that the air that is inhaled by the patient passes through and is filtered by the surface filter;

wherein the surface filter is a filter;

wherein the surface filter forms a fluid permeable barrier that is adapted to allow the flow of air to enter the protected space formed by the nose guard frame;

wherein the surface filter is adapted to filter the air that enters the nose guard frame for inhalation by the patient;

wherein the surface filter is adapted to filter the air that is inhaled by the patient.

7. The eye and nose protection assembly according to claim 6 wherein the right temple strap further comprises a right hose rouleau;

wherein the right hose rouleau is a negative space that is formed through the right extension;

wherein the left temple strap further comprises a left hose rouleau;

wherein the left hose rouleau is a negative space that is formed through the left extension.

8. The eye and nose protection assembly according to claim 7 wherein the right hose rouleau is geometrically similar to the right hose;

wherein the right hose rouleau is sized such that the right hose inserts through the right hose rouleau;

wherein the right hose rouleau guides the right hose from the posterior right side of the patient to the nose guard frame;

wherein the right hose discharges the transported therapeutic oxygen directly into the portion of the protected space that is formed by the nose guard frame.

9. The eye and nose protection assembly according to claim 8 wherein the left hose rouleau is geometrically similar to the left hose;

wherein the left hose rouleau is sized such that the left hose inserts through the left hose rouleau;

wherein the left hose rouleau is adapted to guide the left hose from the posterior left side of the patient to the nose guard frame;

wherein the left hose discharges the transported therapeutic oxygen directly into the portion of the protected space that is formed by the nose guard frame.

* * * * *